United States Patent [19]

Sikiric et al.

[11] Patent Number: 5,288,708
[45] Date of Patent: Feb. 22, 1994

[54] PHARMACOLOGICALLY ACTIVE SUBSTANCE BPC, THE PROCESS FOR ITS PREPARATION AND ITS USE IN THE THERAPY

[76] Inventors: Predrag Sikiric, Jurisiceva 5; Marijan Petek, Visnjica 29; Ivo Rotkvic, Cvjetno naselje 1/21, all of 41 000 Zagreb; Stjepan Mise, Ruzveltova 37, 58 000 Split; Simun Krizanac, Platana 8, 41 000 Zagreb, all of Yugoslavia; Ivan Udovicic, Ennetmooserstraase 16, 6370 Stans, Switzerland; Ernest Suchanek, Aleja V. Popovica 125, 41 000 Zagreb, Yugoslavia; Marko Duvnjak, R. Luxenburg 4, 41 000 Zagreb, Yugoslavia; Jerka Jukic, Palih Omladinaca 33, 41 000 Zagreb, Yugoslavia

[21] Appl. No.: 690,954
[22] PCT Filed: Sep. 11, 1990
[86] PCT No.: PCT/EP90/01533
 § 371 Date: May 10, 1991
 § 102(e) Date: May 10, 1991

[30] Foreign Application Priority Data

Sep. 12, 1989 [YU] Yugoslavia .......................... 1760/89

[51] Int. Cl.[5] .................. C07K 3/28; C07K 15/06; A61K 37/02
[52] U.S. Cl. ..................................... 514/21; 530/344; 530/416; 530/417
[58] Field of Search ............... 530/344, 416, 417, 350, 530/843; 514/21; 424/551

[56] References Cited

FOREIGN PATENT DOCUMENTS 1963816 7/1970 Fed. Rep. of Germany .

Primary Examiner—Howard E. Schain
Assistant Examiner—Lynn Touzeau
Attorney, Agent, or Firm—Anderson Kill Olick & Oshinsky

[57] ABSTRACT

A new substance BPC; the process for its preparation from human and animal gastric juice comprising purifications steps: centrifugalization, dialysis, ion-exchange, chromotagraphy, gal chromatography and lyophilisation; a drug for human and veterinary use and a process for the treatment of stress-induced diseases and disorders, inflammation and edemas, diseases and disorders of dopaminergic etiology, for treatment of diabetes mellitus, diseases and disorders of gastrointestinal tract, heart, kidney, pancreas, liver, testis, hematopoetic, skeletal and nervous, system, dementias, wound, burns, fracture, viral diseases, malignancy; in surgery; some disorders of fertility and immune system; protection against ionizing radiation; for veterinary use in commercial breeding.

4 Claims, 2 Drawing Sheets

PHARMACOLOGICALLY ACTIVE SUBSTANCE BPC, THE PROCESS FOR ITS PREPARATION AND ITS USE IN THE THERAPY

BACKGROUND OF THE INVENTION

1. Field of the Invention

The present invention relates to a new substance BPC, the process for its preparation from human or animal gastric juice and its use in the therapy.

2. Description of the Prior Art

Gastric juice, considered as a secretion of the parietal as well as other cells, contains a number of electrolyte components, hydrochloric acid, a number of enzymes, namely, pepsin, other proteinases, rennin, lipase, urease and lysozyme. There are present many peptides and peptide fragments, e.g. peptide hormones gastrins, a highly potent gastric secretion stimulants, first discovered by J. S.Edkins, Proc.Roy.Soc.L., 76B, 376 (1905).

In normal gastric juice are present glycoproteins (mucins), desribed by F.Hanrowitz, Chem. and Biology of Proteins, 1950, p.199., and Intrinsic Factor (IF), which is a thermolabile mucoprotein with M.W. about 60.000. This factor promotes vitamin $B_{12}$ absorption, Castle et al, Am.J.Med Sci. 178, 748 (1929).

Till now, a substance having very strong antistress actions and other body-protection activities was not found in gastric juice.

DESCRIPTION OF THE INVENTION

Until now the gastrointestinal tract, especially stomach, was considered only as a target organ for stress. There was never discussed the possibility that gastrointestinal tract, preferably the stomach, may be the organ which can initiate the defensive response of the whole organism. This response, actually directed against stress, must be realized in the formation and release of a new endogenous agent. Our attempt was directed to isolate this agent from stomach juice. Finally we isolated the expected substance from the stomach juice of 542 patients. This substance was nominated with abbreviation BPC which means: Body Protection Compound.

The structure of this substance is very complex and after our investigation until now can be characterized as folded protein with partial sequence from N-terminus:

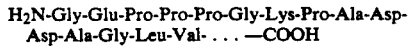

H$_2$N-Gly-Glu-Pro-Pro-Pro-Gly-Lys-Pro-Ala-Asp-Asp-Ala-Gly-Leu-Val-....—COOH

It has a molecular weight of about 40.000±5.000 Daltons, determined by gel filtration.

The agent BPC was prepared from human or animal gastric juice. This juice was first homogenized and centrifuged, the supernatant was purified by dialysis, ion-exchange chromatography, again by dialysis and lyophilisation and finally the agent BPC was obtained using gel-chromatography, dialysis and lyophilisation.

Until now this compound, has not been described or published anywhere Moreover, it has never been used as a medicament.

Figure 1:
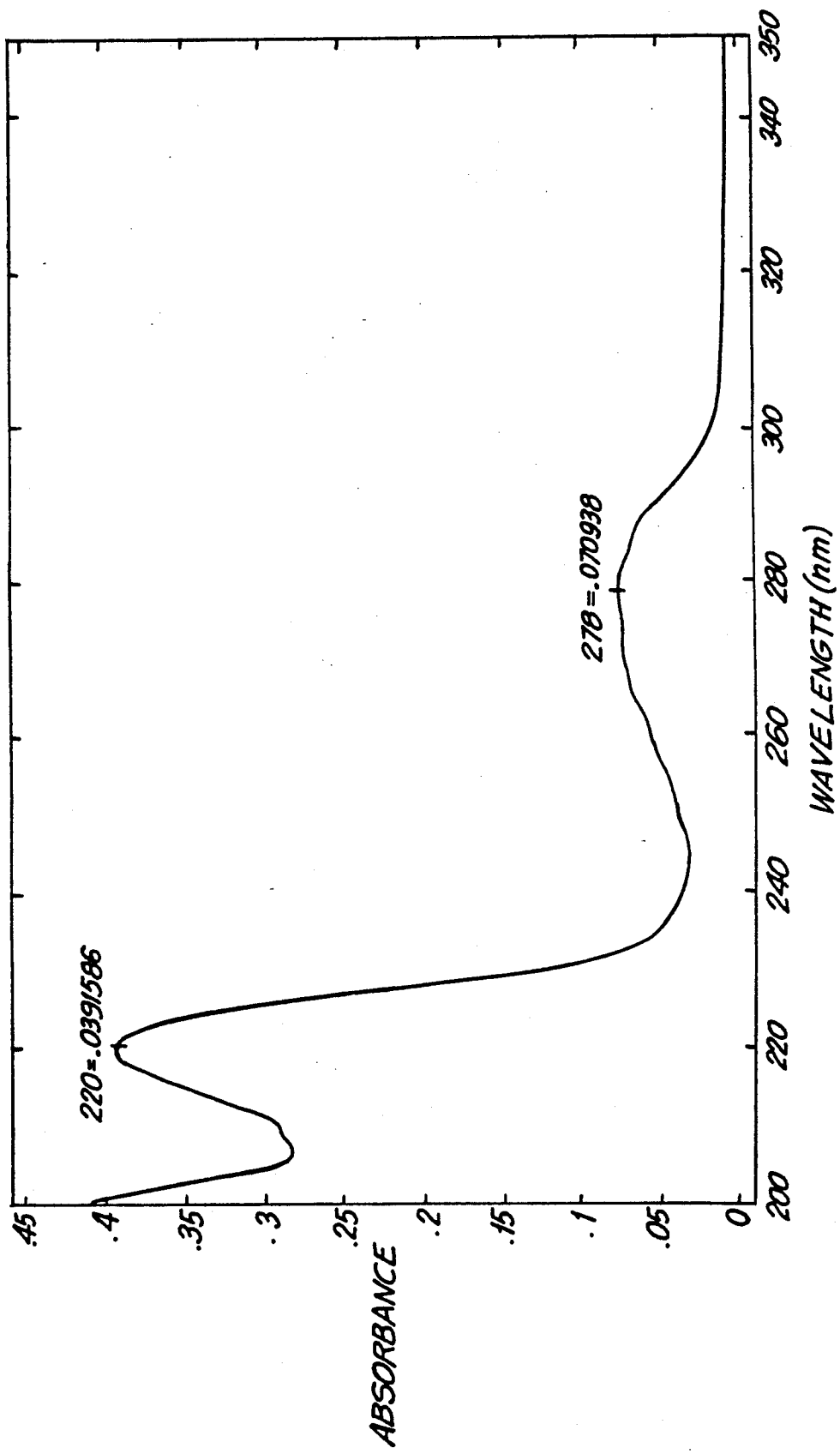
FIG. 1 shows the UV Spectrum of BPC and
FIG. 2 shows the IR Spectrum of BPC.

The investigation of the biological actions of the BPC using many methods in vivo and in vitro shows:

SURPRISINGLY BROAD SPECTRUM OF ACTIVITIES

But, it is known that many diseases and pathological states can be awakened by stress or on the other hand the trauma or disease can induce stress itself. These results also suggest that BPC is produced by stress independent of its provenance.

The agent BPC according to the invention was investigated in vitro and in vivo (rat, mouse, rabbit and guinea-pig) and following pharmacological properties were found:

1. Acute toxicology

Acute toxicology was determined in mice (18-25 gb.w.) (sacrifice after 30 days of experimental period) of both sexes, BPC was administered via i.v. and i.g.. The lethal dose couldn't be obtained even with high dose such as 100 mg/kg b.w., which is at least $10^3$-$10^5$ fold higher than minimal effective doses. In prolonged procedure BPC was injected via i.p., i.v., i.g. (30 mg/kg) once a day over 30 days. No pathological signs (morphological or physiological) were registered. In addition, the mean effective doses are from 0.01 to 50 ug/kg by i.p. administration and TI at least 1000.

2. Ulcer induced by water immersion or restraint stress

Male rats (180-240 g) of Wistar strain were used. Animals were put in cold water (26° C.) for 3 hours or restrainted for 48 hours. After the end of experimental periods the stomach was investigated for the presence of a lesions ("stress ulcers"). The BPC was injected i.p. and intragastrically (0.1 to 10 ug/kg) one hour or 24 hours before of injury induction. A strong protective action of BPC was demonstrated on gastric lesions.

3. Ulcer induced by ligation of bile duct and hegatic artery or cysteamine administration The ligation-experiments were carried out on male rats (160-250 g) of Wistar strain. The ligation of the bile duct and the hepatic artery was performed. This procedure induced besides severe ischemic necrotic lesions of liver tissues, also ulcers of the stomach and duodenum in the intervals from 6-24 hours.

Likewise, cysteamine (400 mg/kg s.c.) was applied for duodenal ulcer induction in female rats in 24 hours period.

BPC was administered i.p. in doses from 0.1-10 ug/kg. The large ulcers induced by described ligation in stomach and duodenum were strongly prevented in BPC treated animals. Likewise, the cysteamine-induced ulcers were also abolished by BPC pretreatment.

4. Effect on infarct induced on myocardium

Male rats (180-230 g) of Wistar strain were immobilizated for 24 hours. The animals were then treated with indomethacin (25 mg/kg s.c.) at time zero of immobilization and 12 hours thereafter. BPC (50 g/kg) was applied one hour before procedure and at 6 hours and 18 hours of restrainted.

In the second group the animal were restraint for 48 hours. After these procedures the animals were sacrified and enzyme values were determined.

The obtained protective actions of BPC were registered.

The protective effects were very impressive. In contrast, there was no protective effect against isoprenaline-induced heart lesions. Isoprenaline (30 mg/kg i.p.)

was applied at zero time and 24 hours later. BPC (50 µg/kg, i.p.) was applied one hour before isoprenaline application. The animals were sacrified 24 hours after second isoprenaline administration and investigated.

5. Effect on arterial tension

Male rats (180–220 g) anaesthetized by urethane were used. The artery carotis was canulated and the blood pressure was recorded on a dynograph. BPC was administered i.v. into v. jugularis in doses of 10 µg to 5 mg/kg. The results showed no changes of arterial tension in animals in a group of rats prepared by above mentioned procedure. A short lasting changes of arterial tension were produced by i.v. administration of noradrenaline, adrenaline, 5-HT, acetylcholine or isoprenaline. The animals pretreated with BPC in doses of 10 ug to 5 mg/kg i.v. showed no changes of arterial tension induced by used vasoactive substances.

6. Effect on damaged liver

The experiments were carried out on male rats (180–250 g) of Wistar strain. The ligation of sole bile duct and of the hepatic artery was performed. This intervention induced severe ischemic necrotic lesions of liver's tissues in the intervals from 6 to 24 hours. BPC was administered i.p. in doses from 0.1 to 10 µg/kg. It strongly prevented (e.g. given 1 hour before ligation) or completely removed the injury (e.g. injected soon after ligation). In addition the liver protective action of BPC administered i.p. in doses of 10 ug/kg of body weight one hour before intoxication of rats with carbon tetrachloride given in doses from 0.1–10 ml/kg i.g. or i.p. was demonstrated. BPC (0.01–10 ug/kg i.p./i.g.) prevented also the fatty liver changes induced by 48 hours of restraint stress.

7. Effect on damaged pancreas

Male rats (170–240 g) of Wistar strain were used. The injury of pancreas was induced by ligation of the bile duct at its point of entry into duodenum. This procedure induced a marked pancreas necrosis 24 hours later and about 50% of rats died within this experimental period. BPC administered in doses from 0.1 to 10 µg/kg i.p. produced a strong and dose dependent protective action. A significant beneficial effect on survival (ca. 82%) was demonstrated.

8. Effect on damaged kidney a. Unilateral nephrectomy

Experiments were carried out on Wistar albino rats (190–250 gb.w.) of both sexes. Unilateral nephrectomy was performed. The increase of the remaining kidney weight was assessed in control and BPC group (10.0 ug/kg b.w. i.p. 1 hour before procedure) 24 hours after surgery. It was demonstrated that BPC strongly decreased the raise in the organ weight of the remaining kidney.

Biochemical parameters were comparable in both groups. Therefore, it seems that BPC does improve the functions of the remaining renal tissue.

b. Administration of gentamicin

Experiments were carried out on the male Wistar rats. Damage of the tubules was produced by administration of gentamicin in dose 40 mg/kg i.p. (once a day) during 30 days. All the animals were sacrified 5 days after the last treatment. In the control group of animals treated with gentamicin and saline, damage of tubuli was found. In the BPC treated group the pathohistological manifestations were significantly smaller.

9. Effect on experimental diabetes mellitus

In male rats (175–230 g) of Wistar strain streptozocin or aloxan induced diabetes mellitus was provoked. The BPC in doses of 10 to 100 µg/kg i.p. tended to delay the streptozocin induced diabetes. Moreover, BPC prolonged the animals survive time significantly.

10. Effect on the fever

Antipyretic activity of BPC was investigated in male rats (180–220 g) of Wistar strain, using injection of the brewer's yeast. The pretreatment with BPC, applied in single doses (5–20 µg/kg i.p.) one hour before injection of yeast significantly reduced the temperature increase calculated at 30 minute intervals for 3 hours at least.

11. Effect on carraeenin induced edemas

The experimental edemas were induced in male mice (18–24 g) of both sexes by injections or carrageenin in the hind paws. The BPC was effective in doses of 10 µg/kg i.p. when injected one hour before the experimental procedure reducing the volume of edemas induced by mentioned agent. In addition, BPC in the same doses was inactive in the (53.5° C.) hot plate test in mice unlike opioid agonists.

12. Effect on experimental rhinitis

Wistar rats of both sexes were exposed to vapour of 10% formaldehyde one hour daily during 15 days. In the test group BpC was administered in doses of 10 µg/kg i.p. on each day one hour before exposition. The animals were sacrified after 13–15 days of treatment. In the BPC treated animals edemas of the nose mucosa were significantly smaller and epithelium was preserved in comparison with control group. Secretion was catarrhal and not purulent.

13. Effect on experimental fracture

The influencce of BPC (10 µg/kg, i.p.) on experimental fracture has been investigated on tibial fracture healing process in rats. With respect to controls, histologic examination showed a significantly increased healing rate in all rats treated subsequently with BPC. In addition, in these animals a markedly lower local haematoma was also registered than in control.

14. Effect on experimental burns

The experimental procedure, involving the treatment of burns of skin or of nasal mucosa, was carried out in mice (20–25 g). In comparison with control group (treated with saline) a purulent secretion was not observed and increased healing rate was consistently noted in all BPC pretreated (10 µg/kg, i.p., one hour before experimental procedure) animals.

In addition, in animals with nasal injury there was also only very modest posttraumatic swelling of the snout. Subsequently the normal nasal respiration was only slightly impared and survival undisturbed. These results are obviously in contrast with the data obtained in the control group.

15. The effect on skin wounds

The experimental procedure was carried out on rats (170–210 g) of Wistar strain. The skin wounds were produced by a large incision of skin. BPC was administered i.p. in single doses of 10 µg/kg before incision.

Unlike the control group, lack of suppuration and edema, poor granulation formation and increased healing rate were consistently found in treated groups.

16. Neuropharmacological activity a) Neuropharmacological investigation according to Irwing demonstrated that BPC, even applied in dosage thousandfold higher than those proven to be of therapeutic effectiveness in many different models (20.0 and 40.0 μg/kg b.w., i.p. or p.o.) did not induce any significant change in behavior on comparison with that in control mice.

b) In the isolated hearts of rat and rabbit, BPC applied in dose 30 μ/ml of Ringer-Locke solution did not induce any change in the intensity and frequency of contraction (preparation according to Langendorf).

c) In the isolated ileum model (rat, guinea pig or rabbit) (preparation according to Magnus), BPC applied in the same dosage did not demonstrate any influence on the intestinal tonus, as well on contraction induced by acetylcholine, histamine and serotinin.

17. The effects of BPC on the delayed type hypersensitivity reaction (DTH) to DNFB The model of DTH reaction to DNFB was used on ears or paws of mice of NMRI strain. Animals which were pretreated with two sensitizing doses of DNFB have significantly thicker ears/paws compared to those of controled animals. Mice pretreated with BPC i.p. in dose of 0.1 μg/10 g of body weight, one hour prior to the application of test dose of DNFB, had significantly smaller differences between treated and nontreated ear/paw.

18. Influence on pupil size

In experiment with mice (18–22 g) of both sexes BPC was instilled in the left eye. The pupil size was measured by means of monocular lens. In addition, one group of animals was treated with BPC administered i.p. The results showed that BPC instilled topically did produce miosis. Also BPC injected i.p. provoked a pupil constriction of about 20%. This effect lasted at least 30 minutes.

19. The effect of BPC on the lesions of the colon

The contact sensitivity in mice was induced with application of DNFB (2,4-dinitrofluorobenzene). Mice was given two sensitizing doses of 25 μl of 0.5% DNFB (in 4:1 acetone: olive oil) on the previously shaved skin of the abdominal wall in two subsequent days. 72 hours after the last sensitizing dose mice were given challenge of 20 ul of 0.2% DNFB, transrectally in ether anaesthesia. Animals were sacrified 24 hours later and the colon has been examined. Pathological changes in colon were characterized with severe hemorrhages and ulcerations. These lesions occupied in some animals all parts of colon wall so that perforations can also occur.

Application of BPC (0.1 μg/10 g) one hour after the DNFB challenge significantly decreases the incidence of lesions in colon. The most common lesion was petechial hemorrhage.

20. Effects on the tumor cells a) Two cell lines L-924 and melanoma B-16 were cultivated in vitro under standard conditions. BPC was tested in vitro on its activity on growing of mentioned cell cultures. Two days following the initiation of cell cultures BPC was added in 3% and 0.3% concentration (0.1 ml). Three days later the numbers of cells per culture were determined by cell counter. The results showed that BPC has an inhibition effect on both cell lines e.g. L-924 and melanoma B-16.

b) Ehrlich's ascites tumor (EAT) is the tumor which can grow in all strains of mice. It can grow in ascitic or in solid form which depends upon a way of administration of tumor cells. We have tried to determine whether the incubation of EAT cells in BPC solution would change the survival time of mice after s.c. or i.p. injection of such treated EAT cells.

We have observed the animals during the period of 45 days. Control of 15 NMRI male mice has been injected with $0.4 \times 10^6$ Eat cells. Prior to the injection tumor cells have been incubated for one hour at 4° C. in saline. Volume of injection was 0.2 ml. Median survival time in this group of animals was 36 days, and only 3/15 animals survived 45 days.

Experimental group of 15 NMRI male mice received the same dose of tumor cells in the same volume, but these tumor cells were previously incubated in BPC solution (2 μg/1 ml). Only 2/15 mice died during the observed period (45 days), the others survived more than 45 days. Difference between the control and the experimental group was significantly different ($p < 0.01$).

If the same procedure has been carried out and EAT cells were injected i.p. (instead of s.c.) no difference between the groups was observed.

It can be concluded that BPC prolonged survival of animals with tumors and that it possesses antitumor effect.

21. Influence on radiation induced injuries

Experiments were carried out on mice (64) of both sexes, NMR-Y strain (22–28) g) First control group (16 mice) was not treated and not irradiated.

The second control group (16 mice) pretreated with saline (0.2 ml) was irradiated with supralethal doses of 9 Gy (Co-60).

Both experimental group (16+16) were irradiated with the same supralethal doses 9 Gy. One hour after irradiation to the first group BPC was administered in doses of 20 μg/kg b.w. However, the second group was treated with the same doses of BPC one hour before irradiation.

BPC administered after irradiation has no influence on the survival of mice.

BPC administered before irradiation increases survival rate after 12 days for 68,75% compared with the other test group.

22. Influence on haematopoetic system

On albino mice were applied cytostatics (Endoxan, Vincristin, Adriablastin, Cytosin-arabinosid) in $LD_{50}$ doses i.p. In test group BPC was applied 1 hour before cytostatics in doses 10 μg/kg, in control group only saline was injected. The group of animals were sacrified on 3, 5, 7 and 11th day of experiment. Investigated were: blood (E,Hb,Htc,L,Tb, abs. number of neutrophiles), bone marrow, cytology and histology of liver and spleen.

On the 3rd day of experiment there is no difference between experimental group regarding L,E,Tb and neutrophile values in comparison to control group. But in bone marrow of BPC treated animals were haemopoetic cells still intact, in control animals aplasia is still present. In the 5th day of experiment there is a significant increase in number of neutrophiles and L until normalisation on 7th day of experiment. In control group the normalisation occurs never before 11th.

23. BPC and fertility—influence on oligoasthenosoermis

The research was performed on ten men ranging in age from 30 to 40 years and having been diagnosed with oligoasthenospermis. From these patients ejaculates were taken after 3 to 4 days of abstinence. After liquefaction (30 min.) to the 0.5 ml of ejaculate is added a layer of 0.5 ml of the medium. The control medium consisted of HAM—F 10 with 10% of desactivated chordal serum.

Experimental medium contained additionally 2 $\mu g/ml$ or 4 $\mu g/ml$ of BPC. After traveling time for 90 minutes at 37° C. in atmosphere containing 5% of $CO_2$, in the Horwell Fertility Chamber was determined the number of progressive movable, movable on place and immovable spermatozoa in 1 ml of ejaculate. Preliminary results show no effect on motility of spermatozoa in lower concentration of BPC. At a concentration of 4 $\mu g$ BPC/ml, a significantly higher % of motility found in comparison with that in the control group.

24. Effect of BPC on reproduction processes

The effect of BPC on reproduction was investigated in mice with previous history of three pregnancies. 20 days after cessation of the last lactation, the animals were subjected to copulation. BPC was applied in a dose 10 $\mu g/kg$ i.p. once daily each day during all period of pregnancy (19–21 days) and lactation (next three weeks). Control group received simultaneously an equivolume of saline. The number of offsprings per female and the weight of offspring were daily recorded.

A careful statistical analysis revealed consistently a significantly increased number of offsprings per female, as well as surprisingly no difference between their body weight at each studied time interval.

All the female animals were allowed to recover for next 25 days after cessation of the lactation. Then, they were again subjected to copulation for investigating the effect on fifth pregnancy.

With regard to control group, an increased fertility rate with increased capability to lactation was registered in all BPC treated animals.

It should be noted that no pathological changes as well as no changes in fertility rate were noted in BPC offsprings (regardless the number of maternal pregnancies).

Therefore, it seems likely that BPC can improve the fertility rate even in quite old mice. For concluding, it is obvious that the obtained results are consistent with overall protective effect of BPC, as well as with the in vitro data obtained using human sperm.

25. The protective action BDC on the periodontal tissues injury

The aim of this research was to investigate the effect of BPC on the root resorption of the periodontal soft tissues induced by mechanical injury of the first molar of the albino rats.

Thirty rats, 4 weeks old, were divided into a control group treated with saline and an experimental group treated with BPC. In all animals we received the following treatments: to practice mechanical injury we used needle like instrument (0.6 mm width and 1.9 mm in length) inserted to 1 mm in depth for 1 sec from the mesial gingival margin in an almost parallel direction to the mesial surface of the first maxillary right molar crown.

Experimental group was treated after mechanical injury with solution of BPC (0.02 ml/200 g). The rats divided in 12 groups were sacrified at interval of 1,3,5,6,14 or 21 days after the final treatment.

The right maxillae of all control and experimental rats were removed, fixed in 10% neutral buffered formaline, demineralized with formic acid, embedded in paraffin and sectioned serially at 6 $\mu m$ in a mesiodistal plane. The sections were stained with haematoxylin and eosin and examined under a light microscope.

Histologic findings in the first molar of the rats from the control groups were: the presence of high number of inflammatory cells was registered. A small resorption lacuna was observed between 1–3 days in part of the root surface at the alveolar crest level. At 5th day, the resorption lacuna extended in a coronal direction. The lacuna contained many odontoclasts. At 7th day, the resorption lacuna with many odontoclasts extended further coronally. At 14th and 21st day, the resorption lacuna still extended coronally, approaching part of the lacuna close to the cementoenamel junction.

Experimental rats had all changes between 1–5 days similar to the control animals, but there was no progress of root resorption between 14–21 day. In conclusion, it can be said that BPC elicited protective action against mechanical injury of periodontal tissues of molar of rats.

26. The influence of BPC on nucleus basalis and spinal cord lesion

Dementia of the Alzheimer type (DAT) is characterized by an acquired global impairment of higher cortical functions which affect memory and cognition. Postmortem studies in patients with DAT have demonstrated that the nucleus basalis (NB) neurons undergo a profound and selective degeneration. These neurons are the major source of extrinsic cholinergic innervation to the cerebral cortex. The purpose of the present study was to investigate the influence of BPC on the passive avoidance behaviour in the rat with bilateral electrolytic lesions of the NB. Namely, rats with lesions of the NB may represent an experimental model of DAT.

The study was carried out on the albino rats. All groups of rats (with or without lesions of NB) were subjected to the passive avoidance test per the procedure of Ashford and Jones. The NB lesioned animals received saline solution (control group) or BPC solution 10 $\mu g/kg$ i.p. (test group).

Tested substances were injected: a) only once, immediately after the NB lesions were made, or b) once a day in the course of four consecutive days after the NB lesions were made. BPC was also administered once per day in the course of four training days, one hour before the passive avoidance experiment started. Each animal was subjected to the described behaviour test after a 20 days lasting postoperative recovery period passed. Statistical significance was calculated according to the analysis of variance combined with Duncan's test for multiple comparisons ($p<0.05$). The results of investigation showed that:

bilateral electrolytic lesions impair the passive avoidance in rats;

BPC in used dosage doesn't influence the passive avoidance behaviour in intact, nonlesioned animals;

BPC can improve the passive avoidance behaviour in the NB lesioned rats significantly.

27. The influence of BPC on the motor activity of rabbits with contusioned spinal cords The aim of this research was to investigate if BPC can modify the consequences of contusioned spinal cord. In present study adjust rabbits of both sexes were used. A medial, dorsal $L_1-L_6$ laminectomy was performed under pentobarbital anaesthesia. By using the Technik of Albin et al a measurable spinal cord compact injury was applied. The motor activity in the hind limbs was controlled in accordance with Tarlov's system once daily during nine days. Basically the ratings were as follows: 1) complete paraplegia, 2) minimal voluntary movements, 3) animal able to stand up, but unable to run, 4) animal able to run with some spasticity and incoordination, and 5) normal motor activity.

Animals were receiving saline in control group and BPC in doses of 10 µg/kg i.v. once per day during nine postsurgery days.

Spinal cord trauma caused almost complete paraplegy. The average of complete (during nine posttraumatic days) tested motor activity in the animals receiving saline was 1.3 Tarlov's units (N=4). In animals receiving BPC it was 2.5 Tarlov's units (N=7).

It is also evident that BPC improved motor activity of rabbits with spinal cord injury.

From presented results it can be presumed that BPC can be a promising drug in the treatment of damaged neuron function (brain or spinal cord trauma) and that BPC should be given as early as possible after neurons are damaged.

28. Influence of BPC on intestine motility, basal temperature and diuresis

Application of BPC doesn't have any influence on diuresis, decreasing of basal temperature in vivo and on the contractibility of intestine smooth muscle of guinea pig in vitro.

29. Activity against Trichinella spiralis

Application of BPC concentrate to experimental mice (Dl) in doses of 10 µg/kg b.w., i.p., previously infected with peroral doses of larvae Trichinella spiralis has the significant influence on survival of animals.

30. Commercial breeding 1419 healthy pigs (from total 4306 pigs) received BPC (10 µg/kg b.w., i.m.) Immediately after birth, other 1440 at 13th day of life 1 day before castration, whereas remaining 1477 received only conventional Fe-therapy. Contusion, culling, mortality, body weight and food consumption were assessed after 4 weeks. BPC, applied only once significantly decreases culling rate (in the group treated with BPC immediately after birth) and contusion rate (in both groups treated with BPC). Same body weight was obtained in BPC treated animals with markedly lower consumption of food.

Influence on infection: 40 weaned pigs affected with E.coli enterocolitis, 28 days old, were investigated. BPC was applied in 20 animals (10 µg/kg b.w. i.m.). One month later a significantly lowering of mortality rate was noted in BPC treated animals.

In an other experiment mortality rate after the first week of life was investigated in a total number of 1200 healthy pigs. 400 animals received BPC immediately after the birth, in addition to conventional Fe-therapy. A significantly lower mortality was noted in BPC (10 µg/kg b.w.,im.) treated animals.

31. Antiviral activity

Antiviral activity was investigated in vitro and in vivo (mice). BPC was used in dose of 10 µg/kg b.w., i.p. or i.e.v. Remarkable activity was found against enteroviruses (Echo type: 6, 9, 11 and 16; Coxsackie type: A9, B3 and B4), CNS viruses (Ixode encephalitis, LCM choriomeningitis) and ARBO viruses (Tahyna, Bhanja, and Calovo).Prolonged survival (72 hours to absolute survival) was noted in infected mice.

In the following text some aspects of the invention will be described in other words:

The technical problem

The technical problem is whether it is possible or not to influence by pharmacotherapy simultaneously:

I
1. acute hepatitis (viral, drugs-induced, toxical, fulminant, regardless ehtiology);
2. chronical hepatitis;
3. liver cirrhosis;
4. cholestasis;
5. cholelelythiasis;
6. cholangitis;
7. liver transplatation—therapy before and after transplatation;
8. therapy before as well as after surgery also in other surgical liver operations (e.g. congenital malformations, benigne and malignant bile duct stenosis);

II
9. prevention of pancreas inflammation;
10. improvement of pancreas inflammation course;
11. lowering of the frequency of postsurgical pancreatitis;
12. prevention of the complications and mortality from acute pancreatitis;
13. lowering the frequency of the chronical pancreatitis III
14. acute hemorrhage in the upper gastrointestinal tract;
15. erosive gastritis;
16. acute ulcer, both gastric and duodenal ("stress ulcer");
17. chronical peptic ulcer;
18. non-peptic ulcer of the gastrointestinal tract;

IV
19. shock (regardless ethiology);

V
20. protection of the renal parenchyma from the development of the acute and chronical ischaemic and haemorrhagic necrosis;
21. acute and chronical renal failure, as well as all causes able to provoke them;

e 2:
VI
22. skeletal trauma (fractures);
23. therapical operation on skeleton (osteotomy),
24. skeletal grafts (calems);
25. pseudoarthrosis;
26. arthrodesis;
27. wounds (increased healing rate, healing "per primam")
28. burns (skin and mucosal , increased healing rate)

VII
29. anti-tumour activity;

VIII
30. antiinflammatory, antiedematous, antirheumatic activity;
31. antipyrrhetic activity;
32. rheumatic arthritis;
33. osteoarthrosis;
34. ankilosans spondilitis;
35. urical arthritis;
36. extra-articular rheumatism (bursitis, tendinitis, synovitis; humeroscapular periarthritis)
37. inflammation and edema after surgical and non-surgical treatment, fracture and dislocation;

IX
38. acute myocardial infarct;
39. myocarditis;
40. delay of the ischaemic changes in the tissues;

X
41. lower food consumption;

XI
42. hyperprolactinemias;

XII
43. M. Parkinsoni, parkinsonism;

XIII
44. glaucoma (decrease of the intraocular pressure —dopamine and pilokarpin like activity);

XIV
45. diabetes mellitus;

XVI
46. barbiturate intoxication;
47. stress and all noxious events developing as the consequence of the stress

The state of the technique

There is still no such total and specific pharmacotherapy, and the treatment of the complications is outside pharmacotherapy.

The description of the solution of the technical problem

Digestive tract and particularly stomach have been presently regarded only as stress-target organ. The possibility suggesting that gastrointestinal tract, and specifically just stomach could also be the organ from which defensive body response may be initiated has not been so far considered. The substance initiating, mediating and controlling the body response, called BPC, has been isolated from the gastric juice of 542 patients, as well as also from animals sources, by means of dialysis, ion-exchange filtration and gel-chromatography. Therefore, the substance BPC (although its structure is not completely clear) is utilized in different models of human diseases, both in vivo and in vitro. On basis of the obtained results, a successful application of extremely wide range could be expected in pharmacotherapy.

The substance, isolated and called BPC, is so far unknown and thereby not applied in pharmacotherapy before.

We have studied the obtained substance BPC on many different experimental species (e.g. rats, mice, guinea pigs) in vivo as well as in human cells in vitro. Substance BPC acronum of the statement: "Body Protecting Compound".

The induction of the damages of the liver, pancreas, stomach and duodenum

In light ether anesthesia a median laparatomy was done. Thereafter, bile duct was ligated distally from duodenum, at the site where hepatic artery (by the same surgical maneuver simultaneously ligated together with bile duct) arrives from the left side, a little below portal vein which remains undamaged above the ligature. Thereafter, the wound was tied, and the animals left undisturbed since death or sacrifice.

In the light ether anaesthesia, a median lapratomy has been done, and bile duct ligated just before its entry into the duodenum. The wound has been thereafter tied, and animals left undisturbed since death or sacrifice.

The animals have been immersed in the water, temperature 26° C., 20 cm of the deep, during 3 hours. Immediately thereafter, they were sacrificed. 24 hours before water immersion, the animals were without food, with free access to water.

In the light ether anesthesia, a median laparatomy has been done and pylorus was ligated. The wound was tied, and the animals undisturbed since sacrifice only 15 minutes after pylorus ligation.

The animals were immobilized for 24 hours. Indomethacin was applied simultaneously with immogilization and 12 hours later. After 24 hours, the animals were sacrified.

The induction of the fracture, wounds, skin and mucosal burns

In the light ether anaesthesia, a tibial fracture was inducted by digital pressure using hipomochlion. The animals were sacrificed at days 5, 8, 9, 12 and 30 after fracture induction.

In the light ether anaesthesia a large skin wound, was induced. The animals were sacrificed each day during first five days, and thereafter after three days periods since 15$^{th}$ day, as well as after the end of the five days periods since one month after wound induction.

In the light ether anaesthesia, a burn has been induced on the back of the animal (15×30 mm) by glowing thermocauter during 15 seconds. The animals were sacrificed at day 5, 9 and 30 after lesions induction.

In the light ether anaesthesia, the nasal mucosa was burned bilaterally by glowing thermocauter during 5 seconds. The animals were sacrificed at day 5, 9, 30 after lesions induction.

The induction of kidney damage

In the light ether anaesthesia, a ligature of renal pedicle has been done. The animals were sacrificed 24 hours later. The wound was tied, and animals undisturbed since death or sacrifice.

The induction of antiinflammatory, antiedemaous and antipyrrhetic effect

Carageenin (1%) was applied (0.05 ml s.c.) in the paw, as inflammatory agent; volume of the paw was measured 3 hours later using the standard procedure.

For elevation of the body temperature the siccoferment was used (2,5 g/kg, i.p.). The temperature was thereafter measured rectally during 3 hours.

The induction of the heart damage

The animals were immobilized during 24 hours. Indomethacin was applied at the start of immobilization (0 hour), and 12 hours latter. After the end of 24 hours period, the animals were sacrificed.

Isoprenaline (30.0 mg/kg i.p.) was applied at 0 and 24 hours, and after the end of 48 hoursperiod, the animals were sacrificed.

The induction of CNS effects the investigation of the effects on spontaneous behavior of the animals (mice)

To establish the presence of dopamine neurons in the activity of the substance BPC in the CNS, a conventional dopamine agonist apomorphine (20 mg/kg s.c.) as well as serotonin (5 mg/kg i.p.) (comparative controls), or saline (0.9% NaCl) (control). The behavior of the animals after applications was investigated. The stereotypic behavior was assessed according to the method of Malick (1983).

the investigation of the effects on the iris muscle

The investigated solution was applied: locally or intraperitoneally. The pupile diameter was measured in the suitable time intervals (5, 10, 15, 30, 60, 90 and 120 minutes) according to standard precedures.

the investigation of the effect on barbiturate depressive activity

With Na-pentobarbital application (50 mg/kg i.v.) a narcosis was induced. The duration of barbiturate sleeping was assessed by the lack or presence of so called "righting reflex".

The induction of the effects on diabetes mellitus

Diabetes mellitus was induced by the application of aloxan (100 mg/kg i.p.) as well as streptozotocin (100 mg/kg i.p.). The glucose content in both urine and blood was measured according to standard procedures. The animals were undisturbed since death.

The assessing of the effects

Distribution

The studies with I-125 marked BPC demonstrate the accumulation of BPC which is also dose and time depending, just in the stomach mostly, with distribution in the whole organism either after oral or parenteral application.

Clinical observation

In the studies dealing with damages of the liver, pancreas, stomach and duodenum, kidney, heart, fracture, wound, burns (skin, mucosal), diabetes mellitus, the general conditions of the BPC treated animals were significantly better than in control groups. Unlike control groups, in the treated groups, either no death or lower mortality rate were consistently observed.

Macroscopical and pathological observations

In the control animals with ligation of the bile duct and hepatic artery a large yellow-green liver necrosis developed, sometimes involving also whole hepatic lobules, as well as pancreas necrosis and haemorrhagic lesions in the stomach and duodenum. The application of BPC successfully and dose-dependently prevented the above described lesions. In the control animals these lesions appeared as soon as 6 hours after ligation, whereas in the treated animals they were not visible even after 48 hours of ligation. Pathohistological examination supported the macroscopically observed changes and differences.

In the control animals with ligation of the bile duct at the site of its entry into duodenum, severe necrosis appeared in the pancreas as well as haemorrhagic lesions in stomach and duodenum. The administration of BPC dose-dependently prevented the development of the above described lesions. Pathohistological examination supported macroscopically observed changes and differences.

In the control animals subjected to water immersion stress, restraint stress plus indomethacin application, as well as short-time (15 min) pylorus ligation, we demonstrated the significant gastric lesions. The administration of BPC markedly decreased (or even completely abolished) the development of the gastric lesions following the above described noxious procedures.

In the control animals with ligature of renal pedicle we found severe lesions of the kidney. In the BPC treated rats the noted lesions were significantly lower. Pathohistological examination strongly supported the macroscopically observed changes and differences.

In comparison with the control animals with tibial fracture, in the BPC treated animals the development of the posttraumatic haematoma was significantly less pronounced, with earlier functional use of the damaged leg. Qualitative pathohistological examination using conventional methods demonstrated increased and exaggerated rate of healing callus in the treated rats in the all observed periods.

In the control animals with wound a large development of the seropurulent granulation was noted during the first days after injury induction. In the BPC treated rats, unlike the control group, it was dry without exudation, with no visible granulations (per primam). Pathohistological examination supported the macroscopically observed changes and differences in all investigated periods.

In the control animals treated with restraint stress plus indomethacin marked myocardial lesions were noted, with increased values of CPK in the serum, the administration of BPC significantly decreased the myocardial damages, and lowered the values of CPK. Pathohistological examination confirmed the macroscopically observed differences and changes.

In the animals with experimentally induced diabetes mellitus BPC abolished transitory glikosuria in the aloxan treated groups. In the animals treated with streptozotocin the administration of BPC almost threefold increased the survival. In all the animals treated with BPC polydipsis and polyfagia were less pronounced.

Antiinflammatory, antiedematous, antipyrrhetic effect

In the animals treated with BPC a marked decrease of the carageenin-induced edema was noted relative to the control in all investigated periods.

In the animals treated with siccoferment, the administration of BPC substance significantly decreased the raise of the body temperature in comparison with the results noted in the control group.

In vitro data

Two days after starting the cultivation of the human fibroblast L-929 and melanoma B-16 cells, the substance BPC was added. Three days thereafter the number of cells was assessed by cell counter. Substance BPC demonstrated a dose-dependent toxic effect on melanoma cells. No effect was demonstrated on fibroblasts.

In comparison with control animal with skin burn, in the treated animals a significantly increased development of the crust was noted. In the control animals with mucusal burns (e.g. nasal mucosa) during first two days a severe edema of the injured tissue was noted, followed with seropurulent secretion, and partial functional obstruction of the nasal respiration. In BPC treated animal no development of the above describe changes was noted. Pathohistological examination strongly confirmed the macroscopically observed differences and changes.

Effects on the CNS

The effects of the substance on the CNS were investigated by observing the behaviour of animals (mice).

5minutes after application a rise in locomotion was observed. The restlesness of the animals increased from minute to minute yielding its peak after 30 min. At that time the animals stood on the hind legs, upright like a candle, and were sniffing. Straubs phenomeonon was evident, the animals were running around the cage and a pyloerection was also obvious. After apomorphine application the change appeared after 45 min., and was accompanied by a partial standing on the hind legs. After serotonin application only a short period of sterotypical behaviour was noted (intensified locomotion, sniffing, cleaning with less intensity).

Local application in the eye resulted (or i.p.) to myosis (aproximately 20%).

The application of BPC shortened the time of barbiturate-induced sleep, which was established by shortening the time without righting reflex (at least 60%).

The effects on blood pressure, cut motility, basal temperature, diuresis

The application of BPC has no effect on the changes of blood pressure induced by adrenaline, noradrenaline, izoprenaline, acetylholine, and serotin, nor on basal blood pressure values.

The application of BPC shows no effect on gut smooth muscle in vitro (guinea pig).

The application of BPC did not lower the basal temperature.

The application of BPC did not lead to increased diuresis.

Mechanism of action

It can be supposed that the action of BPC, like other egzoneous proteins, is a sequella of one of the following mechanism: direct interaction of the protein, or its fragments, with cell receptors; stimulation or inhibition of release of biologically active (stimulatory or inhibitory) proteins or non-proteins, through receptor or nonreceptor linked mechanisms; interactions with enzymes which degrade endogenous biologically active peptides.

Numerous protective effects on otherwise unrelated nosological entities could be explained if they are brought to a common term—the stress (noxis), which they cause in the organism. So it seems likely that the substance BPC represents the primary coping response (starting from the stomach) on any stressful event endangering the organism. Therefore the mechanism of BPC action represents the primary defense mechanism against different stressfull attacks (noxis).

From the above it is concluded that it is possible to act, pharmacologically, beneficially on the course of the following disorders, by the application of BPC:

I
1. acute hepatitis (virus induced, medicamentous, toxic, fulminant regardless the etiology);
2. chronic hepatitis
3. liver cirrhosis;
4. cholestasis
5. choledocholithiasis
6. cholangitis
7. liver transplantation-therapy before and after transplantation
8. preoperative and postoperative therapy in other liver surgery (e.g. congenital malformations, benign and malign stenosis of the choledochus)

II
9. prevention of pancreatitis
10. amelioration of the course of pancreatitis
11. lowering of the rate of postsurgery pancreatitis
12. prevention of complications and mortality of acute pancreatitis
13. lowering of the incidence of chronic pancreatitis III
14. acute upper G tract bleeding
15. erosive gastritis
16. acute ulcers, gastric and duodenal (stress ulcers)
17. chronic peptic ulcers
18. non-peptic ulcers of the GI tract IV
19. shock (all etiology)

V
20. protection of the renal parenchym against ishemic and haemorrhagic necrosis (acute and chronic)
21. acute and chronic renal failure as well as all causes of it VI
22. sceletal trauma (fractures)
23. therapeutic procedures on the skeletal system (osteotomia)
24. skeletal grafting
25. pseudoarthroses
26. arthrodeses
27. wounds (faster healing, healing per primam)
28. burns (skin, mucosa, faster healing)

VII
29. antitumour effect

VIII
30. antiinflamatory, antiedematous, antirheumatic effect
31. antipyrrhetic effect
32. rheumatic arthritis
33. arthroses
34. ankilosing spondilitis
35. gout
36. extraarticular rheumatic disease (bursitis, tendinitis, sinovitis, humeroscapular periarthritis)
37. inflammation and edema after surgical and neurosurgical procedures, accompanying fracture and dislocations XI
38. acute myocardial infarction
39. myocarditys
40. postponing of ischaemic tissue changes X
41. lowering of food intake (anorexitive effect)

XI
42. hyperprolactinaemia
43. Parkinsons disease

XIII
44. glaucoma (lowering of intraocular pressure dopamine and pilocarpine effect)

XIV
45. diabetes mellitus

XV
46. barbiturate intoxication

XVI
47. stress and all stress induced damages of the organism.

The application of the substance will be per os or parenterally, in the form of pills, capsules, dragees, lingualets, suppositories, vaginalets, injection solutions, nasal spray, unguents, creams, gels, spray, eye drops, ear drops, nasal drops.

Examples of technique:

Example 1: process of isolation of the BPC substance

The material from wich the substance was isolated was obtained from the gastric juice of 542 patients repeatedly and reproducibly, and from animal sources. The material was stored at 2'-8° C. The material is homogenised. Than it is centrifugated (12000 G$g$/30 min.). After that the supernatant is collected. 200 ml of supernatant is dialysed in water (+4° C.), 1:125 meaning until a conductibility of 100 $\mu$S is achieved. After that the dyalisate is lyophilised. The dry rest is dissolved in 10 ml of redistilled water and applied onto a chromatographic column with a modified DEAE ion-exchange gel (40–80 um). The column is 25×250 mm. A buffer (Na acetate 0,01 M, pH 5,2) was used for dilution. Fraction detection was by an UV detector in the range of 2800 nm. The fractions of 40–120 ml were collected. The eluate first concentrated by AQUA-CIDE - 3 (Calbiochem, USA) and than lyophilized.

The dry substance in dissolved in 10 ml 0,2 M phosphate buffer, ph 7,4 and than put on 2 chromatograph column with SEPHACRYL-S-200, (2,5×450 mm) with a flow of 1,2ml/min. The fractions of 80–200 ml were collected.

The solution is dialysed against distilled water, concentrated with AQUACID-3 and lyophilized. Approximately 200 mg of a dry, white substance is obtained.

Characterization

Figure 2:
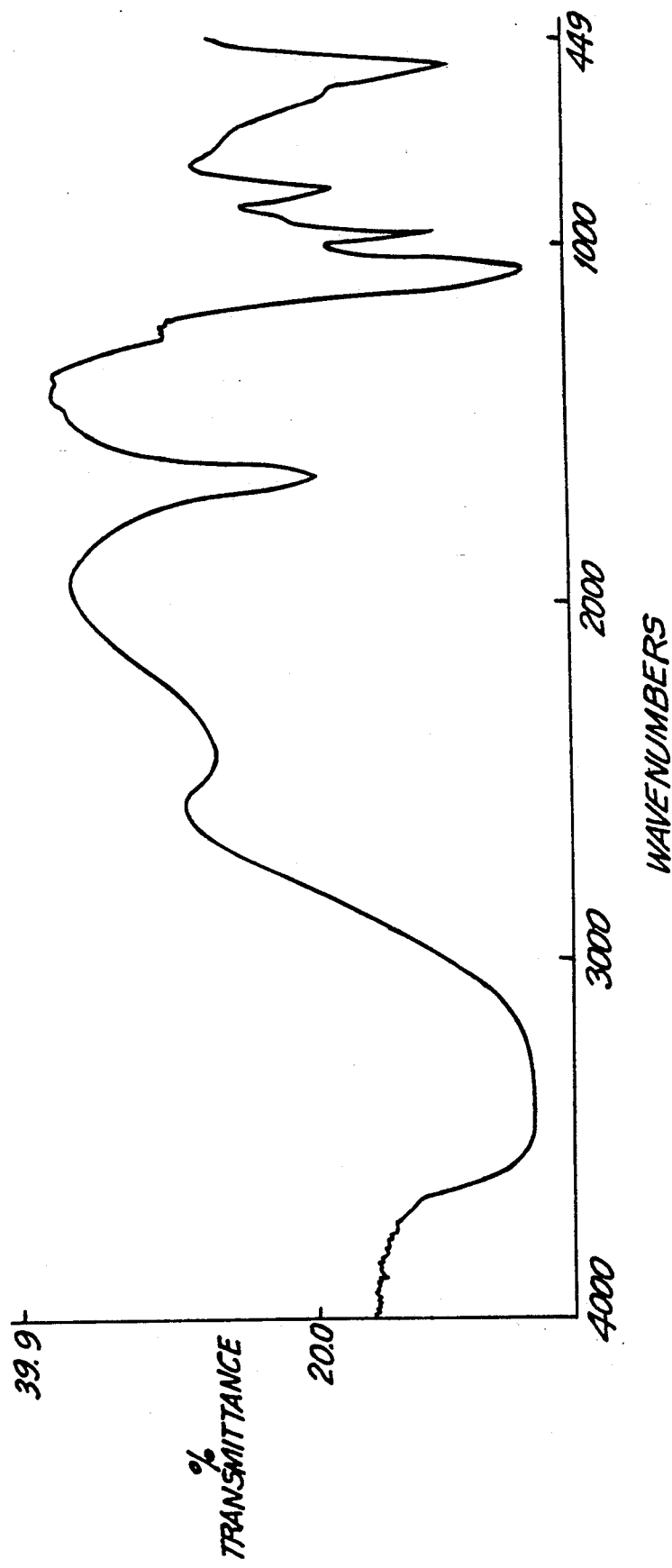

The BPC substance is characterized by IR and UV spectrum (FIG. 1 and 2).

On the basis of the described pharmacological properties the substance BPC can be used in the treatment of several disease and disorders particularly when normal formation of this agent in organism is insufficient or even absent.

It can also be used for the treatment of:
a) All stress induced diseases and disorders.
b) Circulatory disorders:
  Ulcer (different origins), shock (different etiology), Ischemia and infarcts (in different organs).
c) Inflammation and edemas:
  Inflammation and edemas of all etiology, hepatitis (acute and chronic), liver cyrrhosis, cholangitis, pancreatitis (different etiology), gastroduodenitis, nephritis and nephropathias, myocarditis, pericarditis, endocarditis, arthrosis and arthritis, (different etiology), rhinitis, rheumatical disorders-disorders of joint of different ethiology,fever, lesions induced by free radicals.
d) Traumas and surgery:
  Traumatism (pre- and post-traumatic treatment), grafting, wounds, burns, fracture, post-surgery complications.
e) Malignancy: some type of tumors;
f) Diabetes mellitus;
g) Disorders of dopaminergic or similar ethiologv: Obesity, M. Parkinsoni, hyperprolactinemias, glaucomas and barbiturate induced sleep-time (poisoning with barbiturates);
h) Diseases and disorders of nerve system:
  Alzheimer's desease, ischemic and traumatic injuries of the nervous system and delay of senile degenerative changes;
i) Stomatology:
  Diseases and disorders of oral mucosa, surgical treatment of periodontal pockets, inhibition of roots resorption:
j) Haematopoetic system:
  Neutropenia, aplastic anemia, myelodisplastic syndroma transplantation of bone narrow;
k) Injuries caused by radiation:
  Acute radiation syndroma and protection against radiation injuries;
l) Immunology:
  Hypersensitive reactions, allergy and transplantations.
m) Fertility:
  Increasing of fertility, therapy of oligoastenospermia and promotion of lactation;
n) Veterinary use:
  In commercial breeding, decrease of mortality, stunting, contusion, improved conversion of food, increase of body weight;
o) Virusology:
  Antiviral therapy;
  Miscellaneous:
  Fatty change of liver, cholechtasis, cholelithiasis, acute and chronic disfunctions of kidney, toxic damage of kidney and liver Substance BPC will be used as a drug for enteral, local, rectal and parenteral administration. The pharmaceutical compositions are formulated by adding inorganic and organic adjuvants. For tablets and dragees there are added e.g. talc, lactose, starch, stearates etc. for solutions and suspensions there are added e.g. water, alcohols, glycerine etc. For suppositories there are added e.g. natural oils, hardened oils, waxes or polyethylene glycols. The formulations can generally contain suitable preservatives, buffers, stabilizers, surfactants, dissolving intermediaries sweetening agents and dye stuffs.

A suitable daily doses for the substance BPC are from 5 to 50 $\mu$g/kg of weight and can be administered in single doses divided in parts.

Example 1) Preparation of the BPC from human gastric juice

The raw material used for the preparation of the substance BPC was reproducible from stomach juice of 542 patients. The collected material must be stored between +2 and 8° C. It was homogenized before use. An aliquot (200 ml) of this material was first separated by centrifuge (12000 G for 30 minutes) into crude parts and supernatant liquid. This liquid was dialysed against demineralized water (1:125) at +4° C. until the conduction of 100 $\mu$S was attained. Then the solution was lyophilized. The dry residue was dissolved in 10 ml of distilled water and applied onto chromatographic column (25×250 mm) filled with DEAE-modified ion-exchange gel (e.g. Trisacryl M-DEAE, $^R$IBF). For elution sodium acetate buffer (0.01M, OH=5.2 was used. Fractions were controlled with ultraviolet detector at 280 nm. The fractions from the 40th to 120th ml of eluate were collected, concentrated using Aquacid-$^3$R(Calbiochem), then dialysed and lyophilized.

The dry substance was dissolved in 10 ml of 0.2 M phosphate buffer (pH=7.4) and purified again on the chromatographic column (2.5×450 mm) filled with gel Sephacryl-S-200 Pharmacia Fine Chemicals). Flow was 1.2 ml/min. Fractions were collected from the $80^{th}$ to $200^{th}$ ml, dialysed against distilled water, concentrated using Aquacid-3 and then lyophilized. 2 mg of white substance was obtained. The prepared substance—BPC—is very soluble in water. It decomposes between 180° and 200° C. Molecular weight, determined by gel chromatography is estimated as 40.000±5.000 Daltons. The ultraviolet spectrum (in water) shows absorption in regions as indicated in FIG. 1.

The infrared spectrum (in KBr) shows absorption bands in regions as indicated in FIG. 2.

The substance BPC has folded protein structure with partial amino acid sequence from N-terminus:

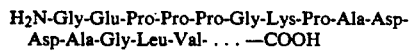

H₂N-Gly-Glu-Pro-Pro-Pro-Gly-Lys-Pro-Ala-Asp-Asp-Ala-Gly-Leu-Val- ... —COOH

Example 2. Preparation of the BPC from human gastric juice

Homogenized human gastric juice of the same provenance as in example 1, was first put in a centrifuge then, dialysed and lyophilised according to the procedure in example 1.

The dry residue (80.4 mg) was dissolved in 0.1 M acetate buffer (3 ml, pH=5.22) and applied onto a chromatographic column (10×50 mm) with ionexchange resin Fractogel-TSK$^R$ (Merck) previously equilibrated with acetate buffer (pH=5.2). Flow was maintained at 0.7 ml/min. Fractions were controlled with UV spectromonitor at 280 nm. First fraction with strong UV adsorbance was collected.

This fraction was dialized against distilled water and then lyophilised (47 mg).

This dry residue was dissolved again in acetate buffer (1 ml) and applied onto chromatographic column (16×560 mm) filled with gel Sephadex-G-100 $^R$ Pharmacia Fine Chemicals) previously equilibrated with acetate buffer. Flow was 0.3 ml/min. Fractions from $66^{th}$ to $108^{th}$ ml, were collected dialyzed against distilled water and lyophilised. A white powder which complies with product described in the previous example was obtained.

Example 3. Precaration of the substance BPC from gorcine gastric juice

Homogenized porcine gastric juice (85 ml) was centrifuge, dialyzed and lyophilised according to the procedure described in previous example to obtain 440 mg of the dry residue. Then 110 mg of this residue was dissolved in 0.1 M acetate buffer (6 ml, pH=5.22) and applied onto chromatographic column (10×50 mm) filled with ion-exchange resin Fractogel-TSK and processed as described in previous example. 44 mg of a yellowish concentrate was obtained.

A part of this concentrate (24 mg) was dissolved in 1 ml of the same acetate buffer and applied onto chromatographic column (16×565 mm) filled with gel Sephadex$^R$—50/80, equilibrated with acetate buffer. Flow was 1.35 ml/min. Eluate between $65^{th}$ and $108^{ml}$ was collected, dialyzed against distilled water and lyophilised. The obtained white powder (10 mg) has (within the range of accuracy and reproducibility of analytical methods used) the same molecular weight and other properties as the product described in previous examples.

| Example 4. Tablets | |
|---|---|
| Composition | mg/tablet |
| substance BPC | 0.3 |
| lactose | 37.7 |
| starch | 6.0 |
| talcum | 3.0 |
| tragacanth | 2.5 |
| magnesium stearate | 0.5 |
| | 50 mg |

| Example 5. Capsules | |
|---|---|
| Composition | mg/capsule |
| substance BPC | 0.3 |
| lactose | 99.0 |
| magnesium stearate | 0.7 |
| | 100 mg |

| Example 6. Lingualettes | |
|---|---|
| Composition | mg/ling. |
| substance BPC | 0.3 |
| mannitol | 100.0 |
| starch | 5.0 |
| polyvinyl pyrrolidone | 1.5 |
| talcum | 3.2 |
| | 110 mg |

| Example 7. Suppositories | |
|---|---|
| Composition | mg/supposit. |
| substance BPC | 0.5 |
| polyethylene glycol 300 | 478.0 |
| polyethylene glycol 1500 | 529.0 |
| polyethylene glycol 6000 | 38.0 |
| emulsifier | 14.5 |
| | 1060 mg |

| Example 8. Cream | |
|---|---|
| Composition | gr/25 gr |
| substance BPC | 0.05 |
| emulsifier | 25.00 |
| hydrogenated oleum arachid. | 50.00 |
| tween 60 | 120.00 |
| propylen glycol | 30.00 |
| methylhydroxy benzoate | 0.16 |
| propylhydoxy benzoate | 0.17 |
| | 250 gr |

| Example 9. Injection solution | |
|---|---|
| Composition | mg/ml |
| substance BPC | 0.3 |
| sodium carboxymethylcellulose | 1.5 |
| polyvinyl pyrrolidone | 5.8 |
| lecithin | 2.7 |
| benzuylalcohol | 0.01 |
| buffer | q.s. |
| bidistillated water ad | 1 ml |

| Example 10. Solution | |
| --- | --- |
| Composition | g/25 ml |
| substance BPC | 0.05 |
| glycerol | 15.00 |
| benzylalcohol | 0.01 |
| buffer | q.s. |
| bidistillated water ad | 25 ml |

| Example 11. Dry injection | |
| --- | --- |
| Composition | weight (mg) |
| substance BPC | 0.3 |
| mannitol | 10.0 |
| | 10.3 mg |

| Example 12. Nasal spray | |
| --- | --- |
| Composition | mg/each dosis |
| substance BPC | 0.5 |
| benzylalcohol | 0.15 |
| uliglyol $^R$-812 | 14.00 |
| freon 12/114 | 60.00 |
| | 74.65 mg |

| Example 13. Drops for eyes, ears and nose | |
| --- | --- |
| Composition | mg/5 ml |
| substance BPC | 45 |
| stabilisator | 5 |
| sodium hydrogenphosphate | 116 |
| sodium dihydrogenphosphate | 33 |
| benzalconium chloride | 0.5 |
| bidistillated water ad | 5 ml |

| Example 14. Vaginalettes | |
| --- | --- |
| Composition | mg/vaginal. |
| substance BPC | 0.3 |
| polyethylene glycol 300 | 150.0 |
| polyethylene glycol 1500 | 1290.0 |
| polyethylene glycol 6000 | 700.0 |
| propylen glycol | 200.0 |
| tween -40 | 59.7 |
| lactose | 100.0 |
| | 2500 mg |

| Example 15. Ophtalmic ointment | |
| --- | --- |
| composition | mg/3.5 gr |
| substance BPC | 45 |
| parrafine oil | 1000 |
| emulsifier | 100 |
| vaseline white | 2355 |
| | 3500 mg |

We claim:

1. A process for preparation of the substance BPC having a molecular weight 40000±5000 Dal and partial N-terminal amino acid sequence: H$_2$N-Gly-Glu-Pro-Pro-Pro-Gly-Lys-Pro-Ala-Asp-Asp-Ala-Gly-Leu-Val—...—COOH from human or animal gastric juice characterized with following production steps in which:

(a) the collected and homogenized animal or human gastric juice is separated in crude parts and supernatant liquid by centrifugalization;

(b) the supernatant liquid is dialysed and lyophilized to obtain a first dry residue;

(c) the first dry residue is purified on a chromatographic column filled with weakly basic modified ion-exchange gel or resin to obtain a first concentrate;

(d) the first concentrate is again dialysed and lyophilized to obtain a second dry residue;

(e) the second dry residue is purified with gel chromatography to obtain a second concentrate and (f) the substance BPC is finally obtained from the second concentrate using dialysis and lyophilisation.

2. The process of claim 1 wherein in the step (c) is used with DEAE, DMAE or AQE.

3. The process of claim 1 or 2, wherein in the step (e) is used an inorganic or organic gel with dextrane, polystyrene, polyacrylamide, agarose, polyvinyl or other matrix but having the fractionation capability in range of molecular weights between 20000 and 100,000 Daltons.

4. The substance BPC prepared by the process of claims 1 or 2 having a molecular weight 40000±5000 Dal., determined by gel chromatography, ultraviolet and infrared spectra as indicated in FIG. 1 and FIG. 2, and partial N-terminal amino acid sequence:

H$_2$N-Gly-Glu-Pro-Pro-Gly-Lys-Pro-Ala-Asp-Asp-Ala-Gly-Leu-Val—...—COOH.

* * * * *

UNITED STATES PATENT AND TRADEMARK OFFICE
CERTIFICATE OF CORRECTION

PATENT NO. : 5,288,708
DATED : February 22, 1994
INVENTOR(S) : Predrag Sikiric, et al.

It is certified that error appears in the above-indentified patent and that said Letters Patent is hereby corrected as shown below:

Column 22:

Claim 4, line 50, column 22, change

" H$_2$N-Gly-Glu-Pro-Pro-Gly-Lys-Pro-Ala-Asp-Asp-Ala-Gly-Leu-Val-...-COOH."

to

-- H$_2$N-Gly-Glu-Pro-Pro-<u>Pro</u>-Gly-Lys-Pro-Ala-Asp-Asp-Ala-Gly-Leu-Val-...-COOH. --

Signed and Sealed this

Twenty-third Day of April, 1996

Attest:

BRUCE LEHMAN

*Attesting Officer*   *Commissioner of Patents and Trademarks*